(12) United States Patent
Lombardo et al.

(10) Patent No.: US 8,741,362 B2
(45) Date of Patent: Jun. 3, 2014

(54) PHYTOCOMPLEX FROM BERGAMOT FRUIT, PROCESS OF MANUFACTURE AND USE AS DIETARY SUPPLEMENT AND IN THE PHARMACEUTICAL FIELD

(75) Inventors: Giuseppe Lombardo, Bianco (IT); Domenico Malara, Bova Marina (IT); Vincenzo Mollace, Bianco (IT)

(73) Assignee: Herbal & Antioxidant Derivatives S.R.L., Polistena (IT)

( * ) Notice: Subject to any disclaimer, the term of this patent is extended or adjusted under 35 U.S.C. 154(b) by 123 days.

(21) Appl. No.: 13/129,637

(22) PCT Filed: Nov. 13, 2009

(86) PCT No.: PCT/IB2009/055060
§ 371 (c)(1),
(2), (4) Date: May 17, 2011

(87) PCT Pub. No.: WO2010/055490
PCT Pub. Date: May 20, 2010

(65) Prior Publication Data
US 2011/0223271 A1    Sep. 15, 2011

(30) Foreign Application Priority Data
Nov. 17, 2008 (IT) .............................. RM2008A0615

(51) Int. Cl.
*A61K 36/752* (2006.01)
(52) U.S. Cl.
USPC .............................. 424/736; 424/777; 514/27
(58) Field of Classification Search
CPC ..... A61K 36/752; A61K 8/498; A61K 8/602; A61K 31/35; A61K 31/3352; A61K 2300/00
USPC ..................................... 424/736, 777; 514/27
See application file for complete search history.

(56) References Cited

U.S. PATENT DOCUMENTS

| 4,439,458 A | 3/1984 | Puri |
| 4,873,095 A | 10/1989 | Rundle |
| 6,409,996 B1 | 6/2002 | Plaschke |

FOREIGN PATENT DOCUMENTS

| WO | 2008/061536 | | 5/2008 |
| WO | WO 2008/061536 A1 | * | 5/2008 |
| WO | 2010/041290 | | 4/2010 |

OTHER PUBLICATIONS

Gattuso et al. "Flavonoid glycosides in bergamot juice (*Citrus bergamia* Risso)" *Journal of Agricultural and Food Chemistry*, vol. 54, No. 11, pp. 3929-3935 (May 2006).
Int'l Search Report for PCT/IE32009/055060, four pages, mailed Jun. 29, 2010.
Written Opinion for PCT/IB2009/055060, five pages, mailed Jun. 29, 2010.
Int'l Preliminary Report on Patentability for PCT/IB2009/055060, nine pages, dated Sep. 28, 2010.
Benavente-Garcia et al. "Update on uses and properties of Citrus flavonoids: New findings in anticancer, cardiovascular, and anti-inflammatory activity" *Journal of Agricultural and Food Chemistry*, vol. 56, No. 15, pp. 6185-6205 (Aug. 2008).
Crupi et al. "Citrus juices technology" in *Citrus: The Genus Citrus* (Dugo et al., eds.), pp. 96-107 (Sep. 2002).
Figoli et al. "Bergamot essential oil extraction by pervaporation" *Desalination*, vol. 193, Nos. 1-3, pp. 160-165 (May 2006).
Gardana et al. "Evaluation of flavonoids and furanocoumarins from *Citrus bergamia* (bergamot) juice and identification of new compounds" *Molecules*, vol. 13, No. 9, pp. 2220-2228 (Sep. 2008).
Gionfriddo et al. "Elimination of furocoumarins in bergamot peel oil" *Perfumer and Flavorist*, vol. 29, No. 5, pp. 48-51 (Jul.-Aug. 2004).
Grohmann et al. "Purification of citrus peel juice and molasses" *Journal of Agricultural and Food Chemistry*, vol. 47, No. 12, pp. 4859-4867 (Dec. 1999).
Kanno et al. "Inhibitory effects of naringenin on tumor growth in human cancer cell lines and sarcoma S-180-implanted mice" *Biological & Pharmaceutical Bulletin*, vol. 28, No. 3, pp. 527-530 (Mar. 2005).
Mandalari et al. "Enzymatic hydrolysis of flavonoids and pectic oligosaccharides from bergamot (*Citrus bergamia* Risso) peel" *Journal of Agricultural and Food Chemistry*, vol. 54, No. 21, pp. 8307-8313 (Oct. 2006).
Miceli et al. "Hypolipidemic effects of *Citrus bergamia* Risso et Poiteau juice in rats fed a hypercholesterolemic diet" *Journal of Agricultural and Food Chemistry*, vol. 55, No. 26, pp. 10671-10677 (Dec. 2007).

* cited by examiner

*Primary Examiner* — Susan Hoffman
(74) *Attorney, Agent, or Firm* — Nixon & Vanderhye PC

(57) ABSTRACT

The invention relates a phytocomplex obtained from the bergamot fruit albedo (*Citrus Bergamia* Risso & Poiteau), the production thereof and the use thereof, in particular under the form of dry extract, to be used as normalizer of the metabolic unbalances of lypemic and glycemic type, in the treatment of the cutaneous diseases with inflammatory or degenerative character, as painkilling/anti-inflammatory agent, as antineoplastic agent and dietary supplement.

16 Claims, No Drawings

US 8,741,362 B2

PHYTOCOMPLEX FROM BERGAMOT FRUIT, PROCESS OF MANUFACTURE AND USE AS DIETARY SUPPLEMENT AND IN THE PHARMACEUTICAL FIELD

This application is the U.S. national phase of International Application No. PCT/IB2009/055060, filed 13 Nov. 2009, which designated the U.S. and claims priority to Italian Application No. RM2008A000615, filed 17 Nov. 2008; the entire contents of each of which are hereby incorporated by reference.

The invention relates to a phytocomplex obtained from the bergamot fruit albedo (in particular a dry extract), a process for the production thereof and the use thereof in the pharmaceutical field and as dietary supplement. If administered by oral route, the phytocomplex has the peculiarity of exerting a normalizing and controlling action with respect to the Cholesterol level, Triglycerides and Glycemia in the blood with consequent strong aterogeneous action. The effectiveness of such action appears even more interesting as directly proportional to the presence of criticality factors in the human organism linked to hyperglycemia and overweight (metabolic syndrome). Furthermore, in the test animal the phytocomplex exerts an antioxidant/anti-inflammatory action which appears both after oral administration, together with a painkilling effect, and, for topic use, after application in areas wherein cutaneous inflammation has been induced. Finally, from studies performed on tumoral lines in culture, the phytocomplex has shown a consistent activity of inhibiting the cell proliferation.

STATE OF ART

Bergamot (*Citrus Bergamia* Risso & Poiteau) is a citrus fruit grown substantially only in restricted areas of Calabria, three main varieties thereof called Femminello, Fantastico and Castagnaro, respectively, are known.

It is known that bergamot represents, within the Calabrese citrus fruit panorama, a particularly precious niche product. In fact, such citrus fruit develops in a limited strip of Reggio Calabria province territory, going from the Tyrrhenian southern side to the Jonic southern side crossing the area of the Messina strait. Therefore, a strip no longer than 150 Km, extending from the more strictly coast area to the pre-hill area of the hinterland of Reggio Calabria. Up to now bergamot has been used exclusively for the properties of the essential oil, particularly requested in perfumery as endowed with an exclusive fragrance which is still being used as basis for preparing several perfumes by the most famous perfume industries and for producing "Acqua di Colonia". This oil is obtained by peeling from the most external portion (cuticola) of the bergamot peel.

It is also known that bergamot has significant antiseptic properties, so that for several years a bergamot derivative, the Bergamon, has been produced and used as disinfectant in the operating rooms. Furthermore, from the traditional medicine the relaxing properties of the bergamot extracts and the important nutriceutic properties of the same are known. At last, the hydroalcoholic solution of the bergamot essence is used for preparing some products (one in particular with the name of Bergarytal), which have been proposed as sprays endowed with the skin's decongestive action and particularly effective in keeping away the mosquitoes. However, the finding that some components of the bergamot essence, such as bergapten, potentially show toxic action has limited the use thereof by requesting procedures for keeping away this compound for the safe use of the essential oil extracts.

The document Gardana Claudio et al "Evaluation of flavonoids and furanocumarins from Citrus Bergamia (Bergamot) juice and identification of new compounds" MOLECULES (BASEL, SWITZERLAND) 2008, vol. 13, no. 9, 18 Sep. 2008 (2008-09-18), pages 2220-2228 is directed only to the study of the content of flavonoids and furanocoumarins in a sample of bergamot juice.

WO 2008/061536 (COSMEDICAL APS [DK]) describes, among other things, compositions for treating the eye disorders with compositions containing also bioflavonoids and a method for extracting such bioflavonoids from bergamot. Such method does not use either pectolytic enzymes or a separation with cationic resins and it does not make reference to the furocoumarin content of the obtained product.

Mandalari Giuseppina et al "Enzymatic hydrolysis of flavonoids and pectic oligosaccharides from bergamot (*Citrus bergamia* Risso) peel" Journal of Agricultural and Food Chemistry, American Chemical Society, Washington, US vol. 54, Nr. 21 1 Oct. 2006 pages 8307-8313 describes the extraction of flavonoids and other compounds starting from the peel of the bergamot fruit, peel considered as sub-product of the essential oil industry.

Gattuso Giuseppe et al "Flavonoid glycosides in bergamot juice (*Citrus bergamia* Risso)" Journal of gricultural and Food Chemistry, vol 54, Nr. 11, May 2006 describes a study developed with the only purpose of differentiating two glycosidates flavonoids contained in a bergamot juice having industrial origin which has been treated with dymethylformamide that is to say a solvent which may not find use in products of medical and/or cosmetic interest.

The present inventors have surprisingly found that, from the bergamot fruit, in particular from the albedo, it is possible to obtain a concentrated phytocomplex showing a great healing action by positively effecting the metabolic activity and by normalizing the lipidic and glycemic levels of the subjects affected by these pathologies. The albedo, in the citrus fruits, is the portion lying between the epidermis including flavedo and pulp and it is formed by cells with tubular structure forming a real net with most part of the tissue volume compressed in the intercellular space. The phytocomplex obtainable preferably under the form of dry extract, thanks to the particular extraction and purification process, has among the components thereof the drastic reduction (up to nearly the elimination) of the furocoumarins existing in the fruit (bergapten and bergamottin) considered potentially toxic substances, at the same time by keeping and even increasing the described healing action.

Therefore, the object of the present invention is the process claimed by claim 1.

The process will better described hereinafter.

Step a (Grinding of Partially De-Oiled Fruit)

The fruit, without the most external portion (Flavedo) and partially de-oiled for removing the outer cuticle, is minced preferably by means of grinding mill in small strips with size smaller than one cm in length.

Step b (Reduction in the Pectin Content)

In the mixture obtained from step a enzymes apt to degrade the pectin, pectolytic enzymes) are inoculated and within 20-40, preferably 30 minutes, with temperature depending from the used enzyme, a much more fluid product is obtained, therefore better workable.

Step c (Separation of the Fibrous Portion from the Liquid Portion):

The product of step b is reduced to a residual pulp content lower than 0.5% advantageously by means of sequential passage on decanter and centrifuge.

Step d (Inactivation of the Pectolytic Enzymes):
Such result will be obtained after pasteurization of the liquid of step c, the pasteurization will have as a secondary effect eliminating by evaporation a remarkable portion of residual essential oils.

Step e (Making Clear the Aqueous Solution):
It is obtained by means of a ultrafiltration process in a plant equipped with semi-permeable membranes with selectivity equal to 12.000 dalton of molecular weight (particles with PM lower than 12.000 dalton go through the membranes). It is also possible, and forms part of the invention, a variant of the process wherein the making clear action takes place by means of treatment with bentonite.

Step f (Adsorption of the Limpid Solution on Columns Containing Polystirenic Absorbing Resins):
The separation of the polyphenols from the remaining solution is obtained by entrapping the same in the pores of the polystirenic absorbing resins having pores with diameter comprised between 100 and 150 Angstrom (ex. SEPEA-BEAD SP 207 Mitsubishi). The polyphenols can be extracted, according to a variant of the process of the invention, also with a mixture of ethyl or methyl alcohol, and ethyl acetate in the ratio 3:1 and recovered by means of subsequent solvent concentration (for example by means of evaporation and subsequent drying).

Step g (Recovery of the Polyphenolic Fraction Entrapped in the Resins' Pores of Step f and Contemporary Lowering of the Furocoumarin Value Up to 400 mg/kg, of Dry Product):
After having performed the outer washing of the resins with hot water at 40° C., in order to eliminate sugars and acids contained in the solution of step e, the recovery of the polyphenolic fraction is carried out by opening such organic compounds, characterized by a circular spatial arrangement, thereby assuming a linear configuration, so to be released from the holes wherein they were trapped. Such effect is obtained by raising the pH up to strongly basic values (pH 12-14). This takes place advantageously by using hydroxides of alkaline metals which also degrade bergapten and bergamottin. Equal effect can be obtained if, instead of using the basic solution, ethyl or methyl alcohol is used. In this case the bergapten and bergamottin degradation would not be obtained.

Step h (Chemical Stabilization of the Phytocomplex in Aqueous Phase):
The polyphenols in the (open) linear form thereof are extremely instable as they tend to be object of oxidative phenomena. It is necessary in very short time to bring them back to the ring-like shape. Such result is obtained by lowering the pH from the value 14 up to strongly acid values (around pH 3). Such effect is obtained by subtracting from the solution cations K+, Na+, etc. This takes place by using strongly cationic resins (ex. Relite CF H+ Mitsubishi). These replace the existing cation with a positive hydrogen (H+). The operation effect is an acidification of the solution up to pH=3 and a subtraction of cations of the used alkaline hydroxide. The result is a product more valuable under the nutritional aspect.

Step i (Physical Stabilization of the Product; "Drying"):
It is obtained by means of removing water, advantageously by evaporation in high vacuum, then at temperatures lower than 60° C. up to complete drying (that is by obtaining a residual humidity lower than 14%). At such humidity values the proliferation of any type of organic contaminant (yeasts, bacteria, etc.) is inhibited. A dry product is obtained.

It is to be underlined that the extraction and purification process allows reducing in drastic manner the contained furocoumarins in (bergapten and bergamottin) which represent a problem in the light of their character of potential toxicity; however found at cutaneous level only and in much higher doses than those found in the juice.

The phytocomplex of the invention, in the form of dry extract, appears like a very fine, hydrosoluble powder, with a yellow-brown colour, with characteristic odour and with bitter taste. It can be encapsulated, put into envelopes, mixed with oils for packaging creams etc. and therefore formulated with pharmaceutically compatible excipients, usual in the formulations of dietary supplements.

An additional object of the present invention is a phytocomplex, preferably under the form of dry extract, obtainable from the albedo of the bergamot fruit according to the process of the invention.

The authors of the present invention have further found—and also this forms object of the invention—that the phytocomplex can be used in the clinical practice and/or as dietary supplement since it has an advantageous ratio between nutritive substances (folic acid, vitamins, etc.) and anti-oxidants (flavonoids in particular) which allows it to be used as antidisipipemic and antiaterogeneous agent. Compositions based upon bergamot dry extract as antidislipemic and/or antiaterogeneous and/or antinflammatory/painkilling topic and systemic agent and/or antitumoral agent containing the phytocomplex of the present invention, advantageously under the form of dry extract, together with additives and/or vehicles of common use in pharmaceutics, are also object of the present invention.

The compositions can be used both in liquid forms and in other forms, lyophilisate, granulate, powder. It has been demonstrated that the phytocomplex performs its healing action for the skin pathologies with inflammatory character if applied by topic route, anti-inflammatory/painkilling action after systemic administration in the test animal and an antiproliferative action on tumoral human cells in culture. Advantageously, dosages ranging from 20 and 40, advantageously 30 mg/kg of body weight, are proposed.

Additional objects of the present invention are dietary supplements based upon the phytocomplex of the invention as adjuvant agents in treatments of antidislipemic and/or antiaterogeneous type and/or for vascular protection.

The phytocomplex of the present invention is a product of natural origin for dietary supplement or pharmaceutical use exerting an action of normalizing the cholesterol level, fats and glycemia in the blood, by means of the combined action of inhibiting the absorption of the cholesterol precursors already at intestinal gastric level, exerted by the polyphenolic fraction contained therein, as well as of inhibiting the activity of 3-hydroxy-3-methylglutaryl CoA (HMG-CoA) reductase in the mammals.

Furthermore, upon studying the effects of the phytocomplex according to the invention it was found, in the test animals, an absolute keeping of the main ematochemical indexes (complete blood count, hepatic transaminase, azotemia and hypercreatininemia) within normality ranges by proving the absence of toxic effects. Such data were confirmed by the absence of steatosic or necrosis phenomena at hepatic and renal level in the treated animals examined post-mortem at microscope. Furthermore, a hystopathological analysis of the brain tissue and of the peripheral nerves proved the absence of induced axonopathies or mielinopathies. The study of the phytocomplex toxicity had the following result: "the toxicologic analysis does not show toxicity factors, according to the legal framework in force". In particular, together with the absence of the common citrus fruit contaminants, it was found the absence of pathological values or however values outside the normal reference values as far as the presence of heavy metals, pesticides, PCB, nitrites and nitrates, dyes, moulds is concerned apart from the absence of ocratoxins, bacterial endotoxins, anaerobic germs and moulds. From the examination of organs (liver, kidney) taken from the guinea pigs, no toxic effect for administrations equal to 80 mg./Kg of body weight/day in the oral administration was noted.

It is to be underlined that the use of hydroxides of alkaline metals, in particular of KOH reduces considerably the quantity of existing furocoumarins and the obtained phytocomplex appears much more concentrated as to the functional aspect.

The phytocomplex object of the present invention is characterized by the biological singleness of the polyphenolic profile having the main Bioflavonoids, in the following percentages:

| | |
|---|---|
| Neoeriocitrin | 29.6% +/− 6.0 |
| Naringin | 32.4% +/− 4.0 |
| Neohesperidin | 38.0% +/− 6.0 |
| Total | 100.0% |

According to the invention, after the step i) of the process, a phytocomplex, under the form of dry extract, is obtained which has a minimum content of neoeriocitrin, naringin, and neohesperidin not lower than 250 gr/kg that is 25%. Furthermore, the furocoumarins meant as bergapten and bergamottin are present in quantities not higher than 400 mg/kg.

Differently from the greatest part of the extracts of flavonoids on the market, the phytocomplex of the present invention is extremely soluble in addition to alcohol also in water at room temperature (20° C.). The analyses of the dry extract have further shown the equivalence with the substances contained in the bergamot juice.

EXAMPLES

The effects of phytocomplex were tested on 100 patients affected by primitive familiar hypercholesterolaemia with and without associated hypertrygliceridemia. The patients were randomized in equilibrated manner between the two sexes (48 males and 52 females), in an age range comprised between 45 and 70 years old. The patients were classified, with respect to the hematic cholesterol LDL levels (cLDL), according to the risk brackets defined by the National Cholesterol Education Programme (NCEP ATP III) of the NHI (National Health Institute). 500 mg/die pills were administered to all subjects for a period of 30 days. The botanic type, used for extracting the phytocomplex, was *Citrus Bergamia* Risso and Poiteau and fruits coming from cultivar Castagnaro, Femminello and Fantastico were used. The treatment lasted 1 month. The patients (32 out of total) who already were taking at the same time statine or other anti-dislipidemic drugs, were invited to continue the already started therapy. At the end of the treatment, the subjects were being observed for 30 days following the end the phytocomplex assumption. The obtained data show the following results:

1) In all subjects, a reduction comprised between 20 and 32% of the plasmatic levels both in the total cholesterol and LDL, with an average increase of 30% in the HDL cholesterol levels was noted.
2) The subjects affected by familiar hypercholesterolaemia, treated only with diet, who had basal plasmatic levels comprised between 230 and 280 mg/dl of cholesterol showed a reduction in the total cholesterol level of 34±4%, of 32±5 in the LDL cholesterol level and an increase in HDL cholesterol level of 28±3%.
3) The subjects affected by familiar hypercholesterolaemia, treated only with diet, who had basal total cholesterol levels comprised between 200 and 230, had a decrease in the total cholesterol plasmatic levels of 28±4%, in LDL cholesterol of 22±2% and an increase of 24±5% in the HDL cholesterol levels.
4) The subjects of the two preceding groups who already were taking statine, had an additional decrease in the total cholesterol plasmatic levels of 20±3%, in LDL cholesterol of 20±4% and an increase in HDL cholesterol of 15±3%.
5) The examined subjects having mixed forms of dislipidemy (hypercholesterolaemia and hypertrygliceridemia) and who were in the range of 40% out of the total (40 out of 100), had an average reduction of 38±6% in the plasmatic levels of triglycerides.
6) The antidislipidemic effect continued to be quite good on the 60th day after interrupting the ingestion of phytocomplex with total cholesterol values on the average equal to 20±2% of the basal values before the treatment.
7) At the end of test, by means of vascular ecodoppler examination the endothelial reactivity was checked, which resulted to have improved on the average by 34±5% in all treated patients, with respect to the control parameters.
8) No substantial variations in the response with respect to sex and age of the examined subjects were noted. Furthermore, the treatment did not cause side effects or pathological variations in the main organ functionality parameters examined clinically or by means of hematochemical examinations, apart from a fairly good reduction in the pressure and glycemia levels in the subjects with alteration of the glycemic metabolism (21%) or hypertensive (24% out of total).
9) An additional effect was studied in test animals (Wistar rat) wherein a painful inflammatory reaction was induced by administration of carragenine in the animal leg. In these animals, both the topical and systemic application of the bergamot phytocomplex induced a reduction in the oedematigeneous inflammatory locoregional reaction with a reduction in the hyperalgesia induced by carragenine.
10) At last, the incubation of the invention phytocomplex with human astrocytoma cells in culture reduced the cellular proliferation, by suggesting the potential use in the antineoplastic sense.

The invention claimed is:
1. A process for production of a phytocomplex from bergamot fruit comprising the following steps:
   a) grinding of the bergamot fruit without its outer cuticle and its flavedo to obtain a non-degraded mixture;
   b) inoculating said mixture with enzymes for degradation of pectin;
   c) reducing to a value lower 0.5% of the pulp content of said mixture obtained from step b);
   d) inactivating said enzymes from step b) to obtain a degraded mixture;
   e) ultrafiltrating said degraded mixture with a membrane having a molecular weight cut off of 30,000 Daltons to obtain a clarified solution;
   f) adsorping polyphenols in said clarified solution onto a column containing polystyrene adsorbent resin;
   g) washing said column having adsorbed polyphenols with water at a temperature comprised between 30°-50° C.

and raising the pH to a value comprised in the interval 12-14 to obtain a first eluate;

h) passing said first eluate on a cationic resin and then lowering the pH to a value lower than 3.0 to recover a second eluate; and i) drying said second eluate to produce a phytocomplex from bergamot fruit in the form of dry extract.

2. A purified solution containing polyphenols and produced by a process comprising the following steps:

a) grinding of bergamot fruit without its outer cuticle and its flavedo to obtain a non-degraded mixture;

b) inoculating said mixture with enzymes for degradation of pectin and reducing pulp content of said mixture to a value lower than 0.5%;

c) inactivating said enzymes from step b) to obtain a degraded mixture;

d) ultrafiltrating said degraded mixture with a membrane to obtain a clarified solution comprised of solutes with a molecular weight of less than 30,000 Daltons;

e) adsorbing polyphenols in said clarified solution onto a column containing polystyrene adsorbent resin;

f) washing said column having adsorbed polyphenols with water at a temperature comprised between 30°-50° C. and raising the pH to a value comprised in the interval 12-14 to obtain an eluate; and g) passing said eluate on a cationic resin and then lowering the pH to a value lower than 3.0 to recover said purified solution containing polyphenols.

3. A method of using a pharmaceutical composition with antidyslipidemic and hypoglycemic effect, containing the polyphenols of claim 2 and pharmaceutically tolerable additives, comprising orally administering said pharmaceutical composition to a subject.

4. A method of using a pharmaceutical composition with painkilling effect on a human being containing the polyphenols of claim 2 and pharmaceutically tolerable additives, comprising administering said pharmaceutical composition to the human being.

5. A method of using a pharmaceutical composition for topical application on a human being with effect on a skin disease containing the polyphenols of claim 2 and pharmaceutically tolerable additives, comprising topically applying said pharmaceutical composition to the human being.

6. A pharmaceutical composition containing as active agent the purified solution according to claim 2.

7. A phytocomplex produced by a process comprising the following steps:

a) grinding of bergamot fruit without its outer cuticle and its flavedo to obtain a non-degraded mixture;

b) inoculating said mixture with enzymes for degradation of pectin and reducing pulp content of said mixture to a value lower than 0.5%;

c) inactivating said enzymes from step b) to obtain a degraded mixture;

d) ultrafiltrating said degraded mixture with a membrane to obtain a clarified solution comprised of solutes with a molecular weight of less than 30,000 Daltons;

e) adsorbing polyphenols in said clarified solution onto a column containing polystyrene adsorbent resin;

f) washing said column having adsorbed polyphenols with water at a temperature comprised between 30°-50° C. and raising the pH to a value comprised in the interval 12-14 to obtain a first eluate;

g) passing said first eluate on a cationic resin and then lowering the pH to a value lower than 3.0 to recover a second eluate; and h) drying said second eluate to produce said phytocomplex in the form of dry extract.

8. The phytocomplex according to claim 7, in the form of dry extract, showing a minimum content of neoeriocitrin, naringin, and neohesperidin not lower than 250 g/kg.

9. A method of using a pharmaceutical composition with antidyslipidemic and hypoglycemic effect, containing the phytocomplex according to claim 7 and pharmaceutically tolerable additives, comprising orally administering said pharmaceutical composition to a subject.

10. A method of using a pharmaceutical composition with painkilling effect on a human being containing the phytocomplex according to claim 7 and pharmaceutically tolerable additives, comprising administering said pharmaceutical composition to the human being.

11. A method of using a pharmaceutical composition for topical application on a human being with effect on a skin disease containing the phytocomplex according to claim 7 and pharmaceutically tolerable additives, comprising topically applying said pharmaceutical composition to the human being.

12. A pharmaceutical composition containing as active agent the phytocomplex according to claim 7.

13. The phytocomplex according to claim 7, wherein said bergamot fruit belongs to a variety selected from the group consisting of Femminello, Fantastico, and Castagnaro.

14. The phytocomplex according to claim 7, wherein in said step b) said enzymes are of pectolytic type.

15. The phytocomplex according to claim 7, wherein in said step h), said dry extract has residual humidity<14%.

16. The phytocomplex according to claim 7, wherein after said step h), said dry extract is ground.

\* \* \* \* \*